US006609393B2

(12) United States Patent
Oakey

(10) Patent No.: US 6,609,393 B2
(45) Date of Patent: Aug. 26, 2003

(54) INTROGEN REJECTION METHOD

(75) Inventor: John Douglas Oakey, Godalming (GB)

(73) Assignee: The BOC Group plc, Windlesham (GB)

( * ) Notice: Subject to any disclaimer, the term of this patent is extended or adjusted under 35 U.S.C. 154(b) by 0 days.

(21) Appl. No.: 10/142,531

(22) Filed: May 9, 2002

(65) Prior Publication Data

US 2002/0194866 A1 Dec. 26, 2002

(30) Foreign Application Priority Data

May 16, 2001 (GB) .............................................. 0111961

(51) Int. Cl.$^7$ ................................................. F25J 3/08

(52) U.S. Cl. ........................................... 62/620; 62/927

(58) Field of Search ............................ 62/617, 620, 927

(56) References Cited

U.S. PATENT DOCUMENTS

| | | | |
|---|---|---|---|
| 4,415,345 A | | 11/1983 | Swallow |
| 4,455,158 A | * | 6/1984 | Vines et al. .................. 62/622 |
| 4,588,427 A | | 5/1986 | Yao et al. |
| 4,690,702 A | | 9/1987 | Paradowski et al. |
| 4,732,598 A | * | 3/1988 | Rowles et al. ................ 62/621 |
| 4,878,932 A | * | 11/1989 | Phade et al. .................. 62/620 |
| 4,934,147 A | * | 6/1990 | Eyre ........................... 62/656 |
| 5,421,165 A | | 6/1995 | Paradowski et al. |

OTHER PUBLICATIONS

"Cryogenic Techniques in Enhanced Recovery of Oil and Gas", by Ruhemann, R., *Indian J. Cryog.*, vol. 9, No. 4, pp. 256–261 (1984).
"Wyoming's Shute Creek Plant Uses NRU Unit", by Pruitt et al., *Oil and Gas Journal*, pp. 78–82, Oct. 9, 1989.
"Plant Design Integrates NGL Recovery N2 Rejection", by Davis et al., *Oil and Gas Journal*, pp. 33–39, Nov. 6, 1989.
"Process and Facility with Particularly High Availability", *Kenneth Mason Publications*, Research Disclosure, No. 397, XP–000726402, pp. 276–279, May 1, 1997.

* cited by examiner

*Primary Examiner*—William C. Doerrler
(74) *Attorney, Agent, or Firm*—Philip H. Von Neida; Salvatore P. Pace

(57) ABSTRACT

A method of forming a methane product by rejecting nitrogen from a feed gas stream comprising methane and nitrogen is disclosed. After being cooled in a main heat exchanger, the feed gas stream is rectified in a double rectification column comprising a higher pressure column and a lower pressure column. A gas flow is recycled from the lower pressure column to the higher pressure column. Part of the recycle flow is compressed in a compressor, cooled, liquefied in a condenser-reboiler and introduced into the higher pressure column. Another part of the recycle flow is also compressed in the compressor, cooled, liquefied in the main heat exchanger or by expansion, and introduced into the double rectification column in liquid state. At least part of the cooling of both parts of the recycle gas is performed in the main heat exchanger. A liquid methane product is withdrawn from the lower pressure column.

10 Claims, 1 Drawing Sheet

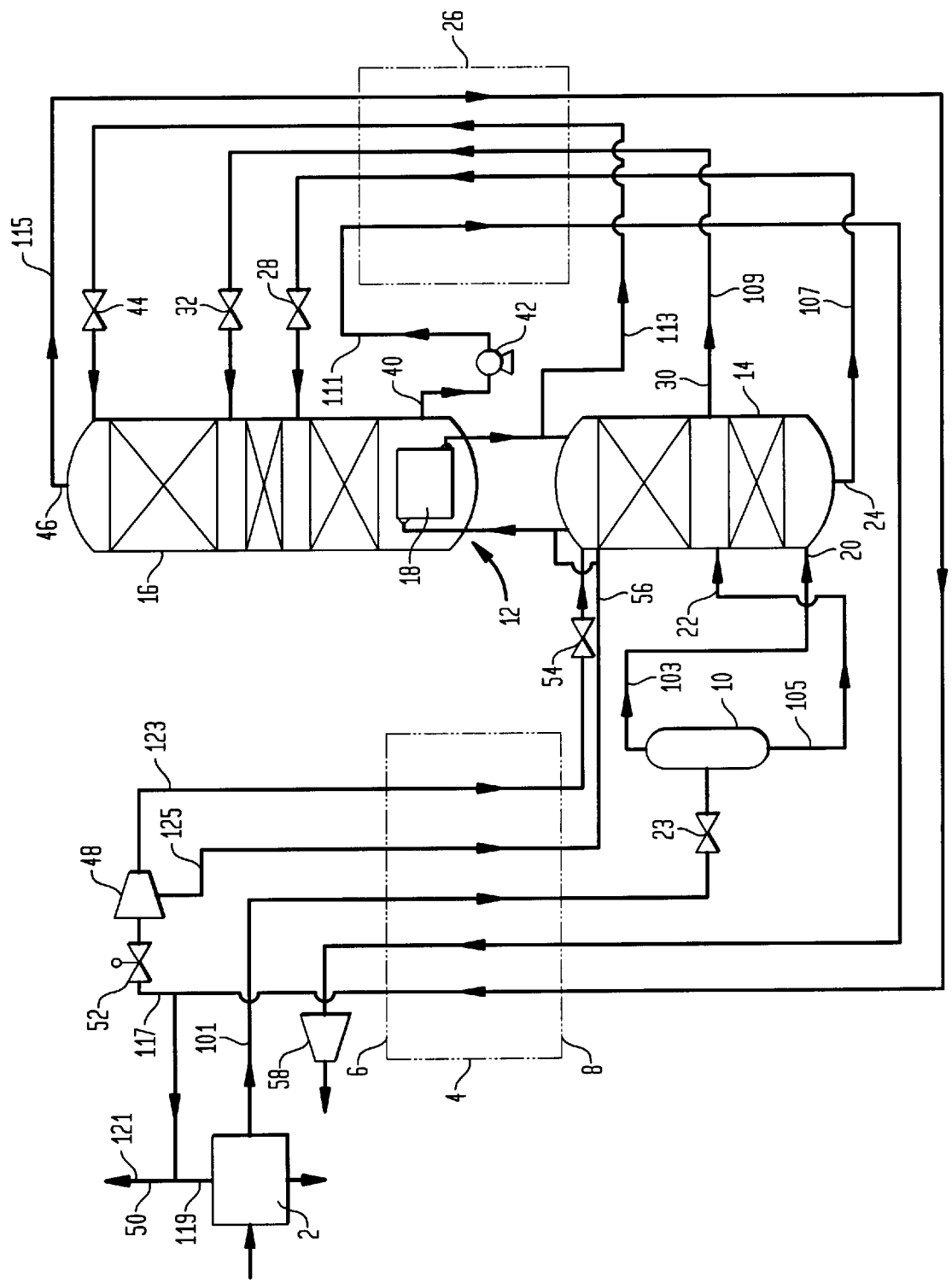

INTROGEN REJECTION METHOD

FIELD OF THE INVENTION

This invention relates to a method of rejecting nitrogen from a feed gas stream comprising methane and nitrogen so as to form a methane product.

BACKGROUND OF THE INVENTION

It is known to produce natural gas from underground reservoirs. The natural gas is often contaminated with nitrogen. The nitrogen may be in part or totally naturally occurring and/or may have been injected into the reservoir as part of an enhanced oil recovery (EOR) or enhanced gas recovery (EGR) operation.

U.S. Pat. No. 4,415,345 discloses a process for rejecting the nitrogen from the methane in a double rectification column operating at cryogenic temperatures. A double rectification column comprises a higher pressure rectification column, a lower pressure rectification column, and a condenser-reboiler placing the top of the higher pressure rectification column in indirect heat exchange relationship with a region, usually the bottom, of the lower pressure rectification column.

In the process according to U.S. Pat. No. 4,415,345 a stream of a mixture of nitrogen and methane at elevated pressure is cooled to a temperature suitable for its separation by rectification. The stream is at least partially liquefied by passage through a condenser-reboiler associated with the bottom of the lower pressure rectification column. A part of the bottom liquid fraction separated in this column is therefore reboiled to provide an upward flow of vapour through the column. Remaining liquid is employed as a feed to the lower pressure rectification column in which a relatively pure liquid methane product is separated as the bottom fraction. A stream of the resulting liquid methane is withdrawn from the lower pressure column and is raised in pressure by a pump. It is warmed by heat exchange to approximately ambient temperature and is thus vaporised.

In order to enhance the liquid nitrogen reflux available to the double rectification column, a stream of nitrogen is withdrawn from the top of the lower pressure rectification column. This nitrogen stream is compressed in a compressor to the operating pressure of the higher pressure rectification column and then combined with a nitrogen stream flowing from the top of the higher pressure rectification column to the condenser-reboiler thermally linking the lower pressure rectification column thereto. As a result, the compressed nitrogen is condensed.

A part of the condensate is returned to the lower pressure rectification column and another part to the higher pressure rectification column. The flow of fluid from the lower pressure rectification to the higher pressure rectification column via the compressor acts as a heat pump. A heat exchanger is incorporated in the heat pump so as to remove heat of compression. This heat exchanger is separate from those in which the pumped product methane stream is warmed.

The vaporisation of the product liquid methane stream in heat exchange with the incoming feed gas stream tends to enhance the thermodynamic inefficiency of the separation method. It is an aim of the present invention to provide a method which makes possible the separation of the feed gas mixture with reduced thermodynamic inefficiency.

SUMMARY OF THE INVENTION

According to the present invention, there is provided a method of rejecting nitrogen from a feed gas stream comprising methane and nitrogen so as to form a methane product, comprising cooling the feed gas stream in a main heat exchanger, rectifying the cooled feed gas stream in a double rectification column comprising a higher pressure rectification column, a lower pressure rectification column, and a condenser-reboiler placing the higher pressure rectification column in heat exchange relationship with the lower pressure rectification column, recycling a flow of gas from the lower pressure rectification column to the higher pressure rectification column, a first part of the recycle gas flow being compressed, cooled, liquefied in the condenser-reboiler, and introduced at least in part into the higher pressure rectification column, withdrawing a product methane stream in liquid state from the lower pressure rectification column, raising the pressure of the liquid product methane stream, and vaporising the liquid product methane stream at least partly in the main heat exchanger, wherein a second part of the recycle gas flow is compressed, is cooled, is liquefied in the main heat exchanger or by expansion, and is introduced into the double rectification column in liquid state, and at least part of the cooling of both parts of the recycle gas is performed in the main heat exchanger.

If its pressure is a sub-critical pressure, the second part of the recycle flow is preferably liquefied in the main heat exchanger. If its pressure is at or above the critical pressure, the second part of the recycle flow is preferably cooled in the main heat exchanger to sufficiently low a temperature that it is liquefied on being reduced in pressure by expansion to the operating pressure of the higher pressure rectification column.

By performing the vaporisation of the product methane and the cooling of the recycle stream in the main heat exchanger, the temperature—enthalpy profile of the streams being warmed in the heat exchanger may be kept closer to that of the streams being cooled therein than in the prior process described in U.S. Pat. No. 4,415,345. As a result, thermodynamic inefficiency is reduced.

Preferably, a vent stream is taken from the recycle gas flow upstream of its compression and is vented according to the invention. Preferably, there is a flow control valve or other means operable to control the size of the recycle stream that is compressed.

There are a number of different options for forming the first and second parts of the recycle flow. In a first arrangement, all the recycle gas is compressed to the same pressure in the same compressor. The recycle gas is partially liquefied, typically by expansion from a supercritical pressure, and a combined flow of liquid and residual vapour is introduced into a top region of the higher pressure rectification column. In a second arrangement, a single, plural stage, compressor is employed. The first part of the recycle flow passes through each stage of the compressor, while the second part of the recycle flow is taken from an upstream stage of the compressor. This second arrangement has the advantage of reducing the work of compressing the recycle gas in comparison with the first arrangement. It is also possible to use separate compressors to compress the first and second parts of the recycle flow.

The second part of the recycle flow is preferably all introduced into the higher pressure rectification column downstream of its liquefaction.

Preferably, for optimum thermodynamic efficiency, a part of the incoming feed gas stream is liquefied in the main heat exchanger. If desired, the resulting partially liquefied feed stream may be subjected to phase separation, the resulting vapour phase being introduced into a bottom region of the higher pressure rectification column and at least part of the liquid phase being introduced into an intermediate mass exchange region of the higher pressure rectification. Preferably, the remainder of the liquid phase is introduced into the lower pressure rectification column at an intermediate mass exchange region thereof. Alternatively, all the liquid phase may be passed into an intermediate mass exchange region of the higher pressure rectification column and a stream of liquid withdrawn from an intermediate region of the higher pressure rectification column and introduced into the lower pressure rectification column.

The pressurised liquid product methane stream is preferably warmed, without being vaporised, in a further heat exchanger upstream of its vaporisation in the main heat exchanger.

Preferably, all the bottom fraction separated in the higher pressure rectification column is withdrawn therefrom and is sent to the lower pressure rectification column. There is therefore no reboiling of this fraction in the higher pressure rectification column.

BRIEF DESCRIPTION OF THE DRAWING

The method according to the invention will now be described by way of example with reference to the accompanying drawing which is a schematic flow diagram of a nitrogen rejection plant.

The drawing is not to scale.

DETAILED DESCRIPTION OF THE INVENTION

A stream of natural gas or gaseous nitrogen-methane mixture is recovered by known means not forming part of this invention from an underground oil or gas reservoir. The stream is typically recovered at a pressure in the order of 40 bar and contains from 10 to 15 percent by volume of nitrogen. The stream may be subjected to preliminary treatment (not shown) in order to remove any hydrogen sulphide or other sulphur-containing impurity therefrom. Such purification of natural gas is well known in the art and need not be referred to in further detail herein.

After removal of any such hydrogen sulphide impurity, the elevated pressure methane-nitrogen stream still typically contains water vapour impurity. The water vapour is removed by passing the methane-nitrogen stream through a purification unit 2, which is shown in the accompanying figure. The purification unit 2 preferably comprises a plurality of adsorption vessels containing adsorbent able to selectively adsorb water vapour from the feed gas stream. Such purification units typically operate on a pressure swing adsorption or a temperature swing adsorption cycle, the latter generally being preferred. If the feed gas stream also contains carbon dioxide impurity, the purification unit can additionally contain an adsorbent selected for carbon dioxide removal so as to effect the carbon dioxide removal.

The resulting purified feed gas stream 101 now consisting essentially of nitrogen and methane flows through a main heat exchanger 4 from its warm end 6 to its cold end 8. The main heat exchanger 4 comprises a plurality of heat exchange blocks preferably joined together to form a single unit. Downstream of the main heat exchanger 4, the feed gas stream 101 is expanded through a throttling valve 23 into a phase separator 10. Depending on its pressure, the feed gas stream is either liquefied in the main heat exchanger 4 or on expansion through the throttling valve 23. Typically, depending on its composition, at least 75 mole percent of the feed gas stream is liquefied. In consequence, the vapour flow is reduced, thus making possible the use of a smaller diameter higher pressure rectification column than would otherwise be required.

The vapour is disengaged, or separated, from the liquid in the phase separator 10. A stream 103 of the vapour phase flows from the top of the phase separator 10 through an inlet 20 into the bottom region of a higher pressure rectification column 14, which forms part of a double rectification column 12 with a lower pressure rectification column 16 and a condenser-reboiler 18 thermally linking the top of the higher pressure rectification column 14 to the bottom of the lower pressure rectification column 16. A stream 105 of the liquid phase flows from the bottom of the phase separator 10 into an intermediate mass exchange region of the higher pressure rectification column 14 through another inlet 22.

Typically the feed gas stream 101 enters and leaves the purification unit 2 at a pressure well in excess of the operating pressure of the higher pressure rectification column 14. As a result, refrigeration is created by passage of the feed stream through the throttling valve 23. This refrigeration meets most of the refrigeration requirements of the method according to the invention and as a result there is typically no need to supply any turbo-expander for this purpose.

The feed gas mixture is separated in the higher pressure rectification column 14 into a vaporous nitrogen top fraction and a liquid methane-enriched bottom fraction. A stream 107 of the methane-enriched bottom fraction is withdrawn from the higher pressure rectification column 14 through a bottom outlet 24 and is sub-cooled by passage through a further heat exchanger 26. The resulting sub-cooled methane-enriched liquid stream flows through a throttling valve 28 and is introduced into an intermediate mass exchange region of the lower pressure rectification column 16.

In addition, a liquid stream 109 comprising methane and nitrogen is withdrawn from an intermediate mass exchange region of the higher pressure rectification column 14 through an outlet 30, and is sub-cooled by passage through the further heat exchanger 26. This sub-cooled stream is passed through a throttling valve 32 and introduced into a second intermediate mass exchange region of the lower pressure rectification column 16 located above the first intermediate mass exchange region.

The streams comprising methane and nitrogen are separated in the lower pressure rectification column 16 in order to form a top nitrogen vapour fraction and a bottom product liquid methane fraction. A stream of the bottom fraction is withdrawn through an outlet 40 from the lower pressure rectification column 16 and is raised in pressure by operation of a pump 42. The resulting pressurised product liquid methane stream 111 is passed through the further heat exchanger 26 countercurrently to the streams being sub-cooled therein. The pressurisation of the product liquid methane stream has the effect of raising its pressure above its saturation pressure. Thus, in effect, the pressurised liquid methane product stream 111 is in sub-cooled state as it enters the further heat exchanger 26. It is warmed in the further heat exchanger 26 to remove the sub-cooling.

It is preferred that no vaporisation of the liquid methane product stream takes place in the further heat exchanger 26. The warmed liquid methane product stream 111 passes from the heat exchanger 26 through the main heat exchanger 4 from its cold end 8 to its warm end 6. It is vaporised as it passes through the main heat exchanger 4. The vaporised methane product is compressed to a desired product delivery pressure in a product compressor 58.

Reflux for the higher pressure rectification column 14 and the lower pressure rectification column 16 is formed by taking nitrogen vapour from the top of the higher pressure rectification column 14 and condensing it in the condensing passages of the condenser-reboiler 18. A part of the resulting condensate is returned to the higher pressure rectification column 14 as reflux. The remainder 113 is sub-cooled by passage through the further heat exchanger 26 and is passed through a throttling valve 44 into the top of the lower pressure rectification column 16 and therefore provides liquid reflux for that column.

A nitrogen vapour stream 115 is withdrawn from the top of the lower pressure rectification column 16 through an outlet 46, and warmed by passage through the further heat exchanger 26. The resulting warmed nitrogen stream is further warmed to approximately ambient temperature by passage through the main heat exchanger 4 from its cold end 8 to its warm end 6. The warmed nitrogen flow is divided into three sub-streams. One sub-stream 117 is compressed in a recycle compressor 48 having a plurality of stages. A second sub-stream 119 of the warmed nitrogen from the main heat exchanger 4 is employed in the regeneration of the adsorbent beds in the purification unit 2. A third sub-stream 121 of the nitrogen is vented to atmosphere through a vent pipeline 50 as a waste stream. The relative size of the recycle stream is determined by the position of an adjustable flow control valve 52 on the inlet side of the recycle compressor 48.

The recycle gas flow entering the compressor 48 is divided into two parts. One stream 123 passes through all the stages of the compressor and flows through the main heat exchanger 4 from its warm end 6 to its cold end 8. The resulting cooled stream of nitrogen is returned to an upper region of the higher pressure rectification column 14 through a throttling valve 54. The nitrogen is typically compressed to a supercritical pressure in the recycle compressor 48 and is cooled in the main heat exchanger 4 to a temperature sufficiently low for it to be liquefied by expansion through the throttling valve 54. However, if it is compressed to a sub-critical pressure, the second part of the recycle flow is preferably liquefied in the main heat exchanger. The flow of this part of the recycle gas through the main heat exchanger 4 helps to match the composite temperature—enthalpy profile of the streams being cooled in the main heat exchanger 4 more closely to that of the streams being warmed therein.

An intermediate pressure stream 125 is also withdrawn from the compressor 48 and is cooled by passage through the main heat exchanger 4 from its warm end 6 to its cold end 8. The intermediate pressure gas remains in gaseous state as it passes through the main heat exchanger 4 from its warm end 6 to its cold end 8. The intermediate pressure nitrogen 125 is introduced into an upper region of the higher pressure rectification column 14 through an inlet 56. The intermediate pressure is therefore chosen to be essentially the operating pressure of the higher pressure rectification column 14.

The part of the recycle gas that flows from the lower pressure rectification column 16 to the higher pressure rectification column 14 via the inlet 56 performs a heat pumping duty which enhances the production of liquid reflux for the rectification columns 14 and 16.

In a typical example of the method according to the invention, the feed gas may be received at a pressure of about 40 bar, the higher pressure column 14 may operate at a pressure at its bottom in the range of 16.5 to 27 bar and the lower pressure rectification column 16 may operate at a bottom in the range of 1.3 to 2.7 bar. The product methane pressure may be in the range of 17 to 28 bar and the nitrogen recycle streams that is liquefied is preferably taken from the recycle compressor 48 at a pressure in the range of 50 to 70 bar.

The large pressure difference between the operating pressure of the higher pressure rectification column 14 and the operating pressure of the lower pressure rectification column 16 does create difficulties in obtaining efficient heat exchange in the heat pump cycle because the difference in the specific heat of nitrogen at the operating pressure of the column 14 and of nitrogen at the operating pressure of the column 16 is quite large. Cooling the nitrogen in the main heat exchanger 4 reduces these difficulties. The resulting improved thermodynamic efficiency can be exploited by, for example, gaining an improved product recovery and/or reviving the pressure at which the product is taken. High recoveries of methane, typically in the order of at least 98.5% are able to be obtained.

What is claimed is:

1. A method of rejecting nitrogen from a feed gas stream comprising methane and nitrogen so as to form a methane product, comprising:

cooling the feed gas stream in a main heat exchanger;

rectifying the cooled feed gas stream in a double rectification column comprising a higher pressure rectification column, a lower pressure rectification column, and a condenser-reboiler placing the higher pressure rectification column in heat exchange relationship with the lower pressure rectification column;

recycling a flow of gas from the lower pressure rectification column to the higher pressure rectification column, a first part of the recycle gas flow being compressed, cooled, liquefied in the condenser-reboiler and introduced at least in part into the higher pressure rectification column;

withdrawing a product methane stream in liquid state from the lower pressure rectification column;

raising the pressure of the liquid product methane stream, and vaporising the liquid product methane stream at least partly in the main heat exchanger;

wherein a second part of the recycle gas flow is compressed, is cooled, is liquefied in the main heat exchanger or by expansion, and is introduced into the double rectification column in liquid state, and at least part of the cooling of both parts of the recycle gas flow is performed in the main heat exchanger.

2. A method according to claim 1, wherein a vent stream is taken from the recycle gas flow and is vented.

3. A method according to claim 1, additionally including the step of controlling the size of the recycle gas flow that is vented.

4. A method according to claim 1, wherein the second part of the recycle gas flow is compressed to a sub-critical pressure and is liquefied in the main heat exchanger.

5. A method according to claim 1, wherein the second part of the recycle gas flow is compressed to at least its critical pressure, and the second part of the recycle gas flow is cooled in the main heat exchanger to a temperature sufficiently low that it is liquefied on expansion to the operating pressure of the higher pressure rectification column.

6. A method according to claim 1, in which the entire second part of the recycle gas flow is introduced into the higher pressure rectification column.

7. A method according to claim 1, in which at least 75% of the feed gas stream is liquefied upstream of the higher pressure rectification column.

8. A method according to claim 7, in which the partially liquefied feed stream is subjected to phase separation into a liquid phase and a vapour phase, at least part of the resulting liquid phase being introduced into an intermediate mass exchange region of the higher pressure rectification column, and the vapour phase being introduced into the bottom of the higher pressure rectification.

9. A method according to claim 1, in which the pressurised liquid product methane stream is warmed, without being vaporised, in a further heat exchanger upstream of its vaporisation in the main heat exchanger.

10. A method according to claim 1, in which a plural stage compressor is used to compress both parts of the recycle gas flow.

* * * * *

UNITED STATES PATENT AND TRADEMARK OFFICE
CERTIFICATE OF CORRECTION

PATENT NO.      : 6,609,393 B2
DATED           : August 26, 2003
INVENTOR(S)     : John Douglas Oakey It is certified that error appears in the above-identified patent and that said Letters Patent is hereby corrected as shown below:

<u>Title page, Item [54] and Column 1, line 1,</u>
Change "INTROGEN" to -- NITROGEN --.

Signed and Sealed this

Ninth Day of December, 2003

JAMES E. ROGAN
*Director of the United States Patent and Trademark Office*